United States Patent
Perez, III et al.

(10) Patent No.: US 9,295,556 B2
(45) Date of Patent: Mar. 29, 2016

(54) MINIMALLY INVASIVE TOTAL HIP REPLACEMENT

(75) Inventors: Arley Perez, III, Fort Myers, FL (US); Christopher G. Papangelou, Bonita Springs, FL (US); Gregory Joshua Karnes, Estero, FL (US); Antonio Pozzi, Gainseville, FL (US); Brandon L. Roller, Naples, FL (US)

(73) Assignee: Arthrex, Inc., Naples, FL (US)

( * ) Notice: Subject to any disclaimer, the term of this patent is extended or adjusted under 35 U.S.C. 154(b) by 152 days.

(21) Appl. No.: 13/366,949

(22) Filed: Feb. 6, 2012

(65) Prior Publication Data

US 2012/0203352 A1    Aug. 9, 2012

Related U.S. Application Data

(60) Provisional application No. 61/440,102, filed on Feb. 7, 2011.

(51) Int. Cl.
| | |
|---|---|
| *A61F 2/36* | (2006.01) |
| *A61F 2/30* | (2006.01) |
| *A61B 17/86* | (2006.01) |
| *A61B 17/74* | (2006.01) |

(52) U.S. Cl.
CPC .............. *A61F 2/3601* (2013.01); *A61B 17/74* (2013.01); *A61B 17/86* (2013.01); *A61F 2002/3085* (2013.01); *A61F 2002/30332* (2013.01); *A61F 2002/30367* (2013.01); *A61F 2002/30405* (2013.01); *A61F 2002/30408* (2013.01); *A61F 2002/30426* (2013.01); *A61F 2002/30604* (2013.01); *A61F 2002/30841* (2013.01); *A61F 2002/30858* (2013.01); *A61F 2002/30892* (2013.01); *A61F 2002/3654* (2013.01)

(58) Field of Classification Search
CPC ..... A61F 2/32; A61F 2/36; A61F 2002/3611; A61F 2002/3625; A61F 2002/365
USPC .......... 623/19.11–19.14, 23.11, 23.27, 23.42, 623/23.43, 20.35, 20.36, 22.4–23.14, 623/22.11–22.2, 23.15–23.38; 128/898
See application file for complete search history.

(56) References Cited

U.S. PATENT DOCUMENTS

| | | | | |
|---|---|---|---|---|
| 5,980,575 | A  * | 11/1999 | Albrektsson et al. ...... | 623/23.11 |
| 2007/0282450 | A1 * | 12/2007 | Habermeyer et al. ...... | 623/19.14 |
| 2008/0033577 | A1 | 2/2008 | Kohan | |
| 2008/0234401 | A1 | 9/2008 | Papangelou et al. | |
| 2008/0306601 | A1 * | 12/2008 | Dreyfuss .................... | 623/19.14 |

FOREIGN PATENT DOCUMENTS

EP        1656910 A1 *  5/2006   ............... A61F 2/40

* cited by examiner

*Primary Examiner* — Christopher D Prone
(74) *Attorney, Agent, or Firm* — Blank Rome LLP

(57) ABSTRACT

A femoral implant for total hip replacement includes a cage screw, a femoral head and a base plate provided between the cage screw and the femoral head, to minimize the stress transferred from the femoral head to the bone. The femoral implant may optionally include devices for lateral fixation (for example, internal and/or external screws for lateral fixation) and a device for minimizing micro-motion that is integral to, and extends from, the cage screw.

3 Claims, 27 Drawing Sheets

MINIMALLY INVASIVE TOTAL HIP REPLACEMENT

CROSS-REFERENCE TO RELATED APPLICATIONS

This application claims the benefit of U.S. Provisional Application Ser. No. 61/440,102, filed Feb. 7, 2011, the entire disclosure of which is incorporated by reference herein.

FIELD OF THE INVENTION

The present invention relates to a hip prosthesis and methods of reconstruction of the femoral acetabular joint with particular application for humans and canines.

BACKGROUND OF THE INVENTION

Hip replacement surgery repairs severe hip damage. In a hip replacement, the surgeon removes degenerate cartilage and bone from the hip joint and replaces them with prosthetics. The ball-and-socket hip joint is replaced with an artificial implant. The materials used in the implant depend on several factors, including the age of the patient, the activity level of the patient, and the surgeon's preference. Hip replacement can relieve pain, help the hip joint work better, and restore normal walking and other movements.

Various prostheses have been designed to mimic the portion of the hip joint or joint region being replaced. A total hip replacement modular prostheses, for example, includes a long stem or screw to be anchored in the femoral side of the total hip and a femoral head that engages the stem or the screw. During use, the stress on the femoral head is transferred onto the long stem or screw which, in turn, may create considerable damage into the bone and fracture through the bone around the level of the tip of the stem or screw.

SUMMARY OF THE INVENTION

The invention provides a minimally invasive total hip replacement. The invention provides a novel prosthetic assembly for prosthetic and surgical methods for reconstitution of a joint, with special applications to the acetabulofemoral joint of humans and canines. The prosthetic assembly includes a femoral implant that comprises a cage screw, a femoral head and a base plate provided between the cage screw and the femoral head, to minimize the stress transferred from the femoral head to the screw. The femoral implant may optionally include at least one screw for lateral fixation (internal and/or external screw(s)); and/or a device for minimizing micro-motion that extends from the cage screw.

The present invention also provides methods of conducting minimally-invasive hip surgery by providing a prosthetic assembly comprising a femoral implant fixed within a socket formed in the femur.

These and other features and advantages of the invention will be more apparent from the following detailed description that is provided in connection with the accompanying drawings and illustrated exemplary embodiments of the invention.

DETAILED DESCRIPTION OF THE INVENTION

Figure 1A:
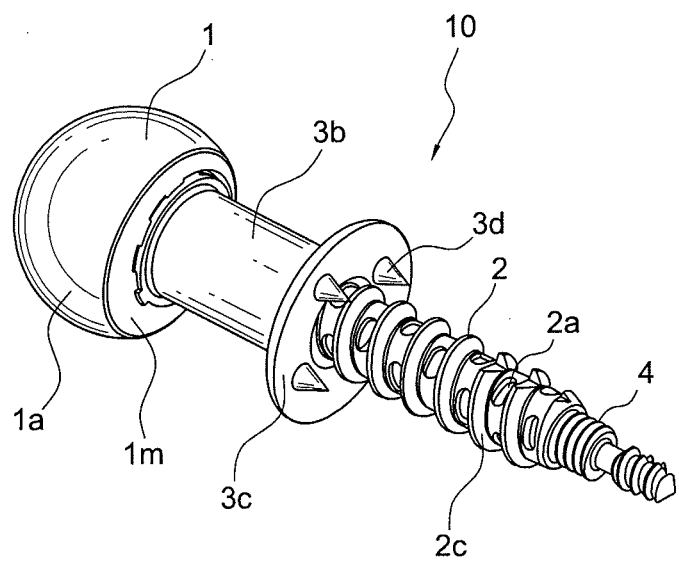
FIG. 1A illustrates a perspective view of a femoral implant according to a first embodiment of the present invention (consisting of a cage screw, base plate including a neck, internal screw for lateral fixation, and femoral head)

The invention provides prosthetic assemblies for prosthetic and surgical methods for reconstitution of a joint, with special applications to the hip joint. As detailed below, the prosthetic assembly includes a femoral implant that is configured to be inserted in a socket formed in the femur.

Referring now to the drawings, where like elements are designated by like reference numerals, FIGS. 1A-10 illustrate various exemplary embodiments of femoral implant 10, 10a, 100, 100a, 200a, 200b, 300 of the present invention with a femoral cap/head having a spherical, partial eclipse-type configuration. The femoral implant consists of a cage screw, a base plate (configured to situate the cage screw on the base plate) and a femoral head that engages the base plate (but not the cage screw), with optional lateral fixation (which may be internal and/or external) and with an optional device for minimizing micro-motion (the device acting like a stop and extending from the cage screw).

FIGS. 1A-2C illustrate views of an exemplary femoral implant 10, 10a consisting of cage screw 2, base plate 3, device 4 for lateral fixation (for example, a screw), and femoral head or cap 1.

Cage screw 2 can receive (i) an internal screw 4 for lateral fixation; and/or (ii) an external screw for lateral fixation. Cage screw 2 can be fenestrated (with a plurality of fenestrations, holes, apertures or openings 2a, shown in FIG. 1B) and can be porous coated at strategic locations. Cage screw 2 can be used as lateral fixation, and be provided with cannulation 2b (FIG. 1B) or without cannulation. The plurality of fenestrations or holes 2a formed through the body of the screw 2 permit the passage of ingrowth bone, or of any bone growth material(s) and/or bone material(s), or of any fixing material (such as acrylic cement, for example), through the walls of the screw 2, to increase the fixation of the device within the femur. As detailed in FIGS. 1A, 1B, 2A, 2B, screw 2 is provided with threads 2c to allow the insertion and subsequent fixation of the screw (through base plate 3 and with femoral head 1 attached thereto) into the femoral socket or tunnel.

Figure 1B:
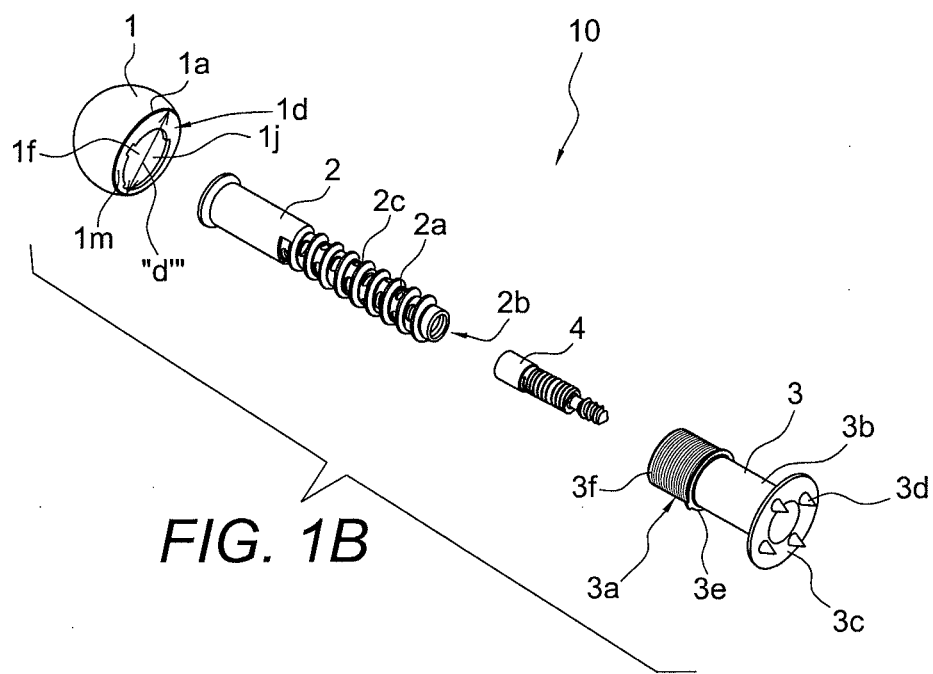
FIG. 1B illustrates an exploded view of the femoral implant of FIG. 1A.
Figure 1C:
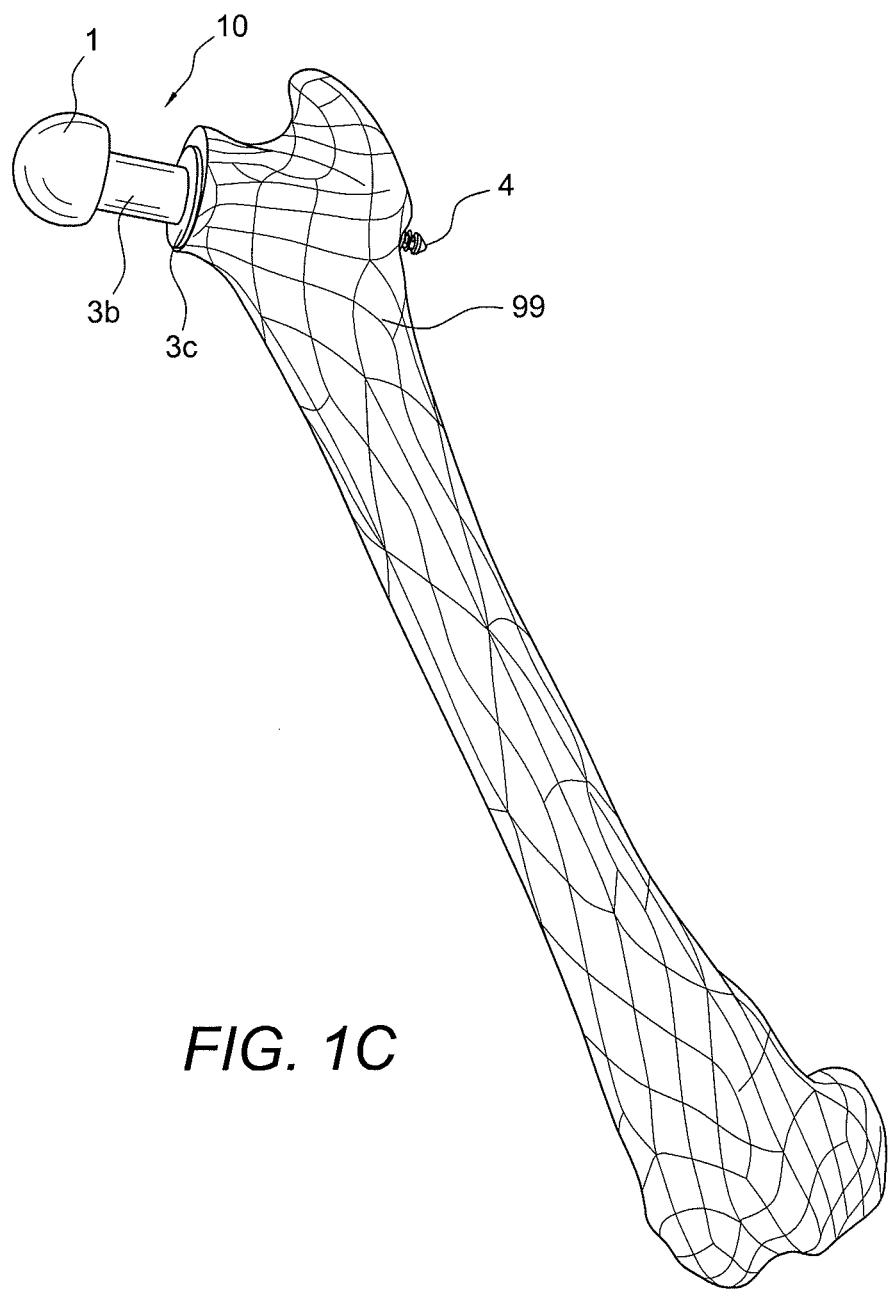
FIG. 1C illustrates a simulated femoral implant (consisting of a cage screw, base plate including a neck, internal screw for lateral fixation, and femoral head) inserted into the femur.

Base plate 3 may have various configurations. In one embodiment, the base plate 3 contains femoral head mating surface 3a, neck 3b, and base 3c (FIGS. 1A-1C). Base plate 3 can further include a key/tab 3e for anti-rotation; can include extensions (spikes or protuberances) 3d from the base 3c to engage into bone; can include grooves/texture/threads 3f on the head engaging surface (for engaging and locking of the femoral head 1); can include an engagement mechanism for engaging the femoral head in the form of a Morse taper, or a tapered shank to be inserted into a tapered opening of the femoral head and pushed or twisted into place, to be retained by friction, for example; can include a porous backing on the base; and/or can include a neck 3b which can be manufactured with different diameters and lengths.

Figure 2A:
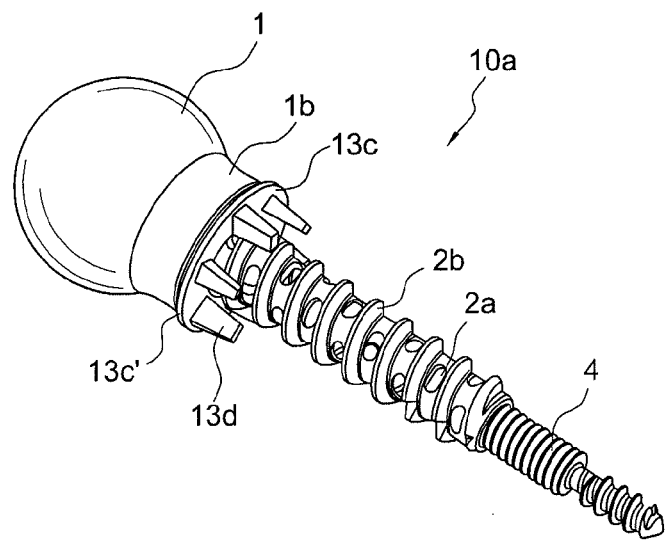
FIG. 2A illustrates a perspective view of a femoral implant according to a second embodiment of the present invention (with the femoral implant consisting of a cage screw, base plate, internal screw for lateral fixation, and femoral head with neck)
Figure 2B:
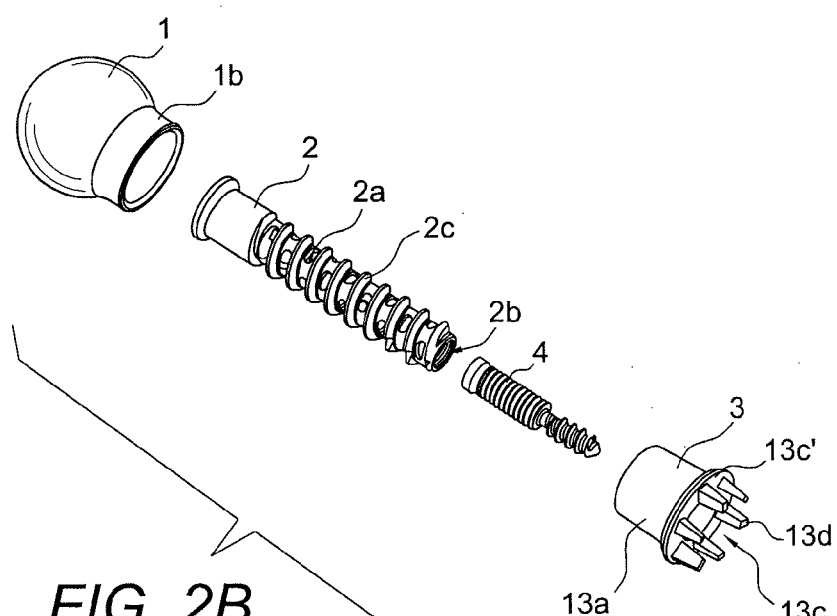
FIG. 2B illustrates an exploded view of the femoral implant of FIG. 2A.

In another embodiment, the base plate 3 contains femoral head mating surface 13a and a base 13c (without a neck), as shown in FIGS. 2A-2C. Base plate can further include a key/tab for anti-rotation; can include extensions (spikes or protuberances) 13d from the base 13c to engage into bone; can include grooves/texture/threads; can include an engagement mechanism for engaging the femoral head in the form of a Morse taper, for example; and/or can include a porous backing on the base. In yet another embodiment, the base plate 30 contains only a base 30c that situates the cage screw 2 on the base plate, as shown in FIG. 6 and FIGS. 7A-7E.

Base 3c, 13c preferably has an outer diameter about equal to the outer diameter of opening 1f of the femoral head 1 (as shown in FIG. 1B, for example) and a thickness of about 1 to about 5 mm, more preferably of about 2 mm to ensure secure placement of the base plate over the remaining, cut surface of the resected femoral head, as detailed below.

Femoral head 1 can be provided with no offset or with offset (as shown in FIG. 1A, for example), and can receive an anti-rotation "key" such as tab/key 3e of base plate 3. In an exemplary embodiment, and as shown in FIGS. 1A-2B, femoral head 1 has a convex configuration (a partial eclipse-type configuration), which is similar to the curvature of the femoral head to allow the implant 10 to reconstruct the anatomy of the damaged femoral head. Convex outer surface 1a (FIGS. 1A-2B) of the femoral head 1 will permit both the full anatomical reconstruction of the femoral head and the introduction of the convex surface within the hip joint cavity. Inner opening 1j with inner surface 1k of the femoral head 1 (which is opposite the outer surface 1a and which faces the bone (the femur) when the femoral head is inserted) receives head engaging surface 3a of the base plate 3, as detailed below. The inner opening 1j of the femoral head 1 securely engages head engaging surface 3a of base plate 3 (with the slot 1d receiving anti-rotation "key" 3e of the base plate 3) (also shown in more detail in FIG. 3I). The dimension and measurements of the femoral head 1 are a function of the patient's anatomy.

Femoral head 1 can further include a neck 1b (cylindrical stem portion) (shown in FIG. 2B) or no neck (shown in FIG. 1B). The neck or cylindrical stem portion 1b extends about perpendicular to the convex outer surface 1a. The neck or cylindrical stem portion 1b of the head 1 is further provided with an internal cylindrical stem area that rests on (abuts) a surface area 13c' of the base 13c (as shown in FIGS. 2A and 2B), when the femoral head is attached to the base plate.

Figure 6:
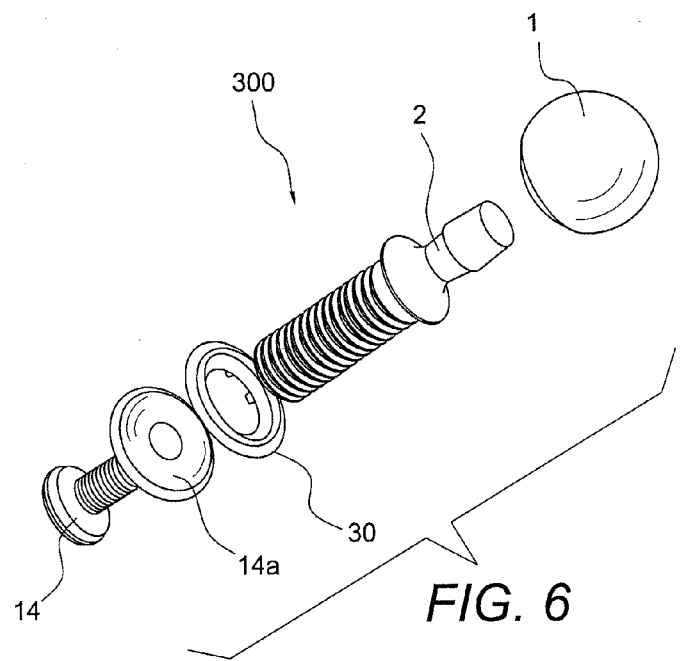
FIG. 6 illustrates an exploded view of a femoral implant according to a fifth embodiment of the present invention (with the femoral implant consisting of a cage screw, base plate, femoral head, and external screw for lateral fixation)
Figure 7A:
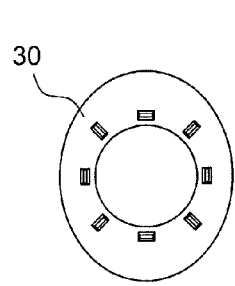
FIGS. 7A-7E illustrate various views of the base plate of FIG. 6 (configured to situate the cage screw on the base plate)
Figure 7B:
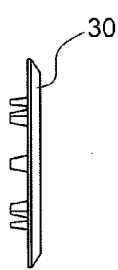
Figure 7C:
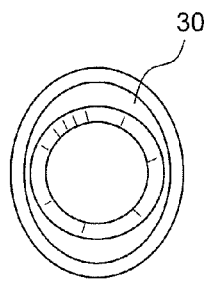
Figure 7D:
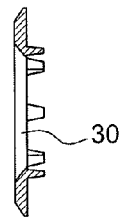
Figure 7E:
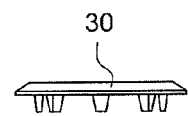
Figure 8A:
FIGS. 8A-8F illustrate various views of the configuration of washer and screw of FIG. 6 for external lateral fixation.
Figure 8B:
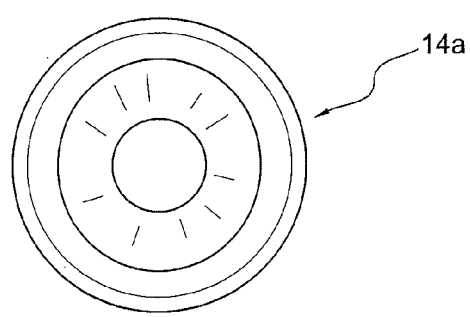
Figure 8C:
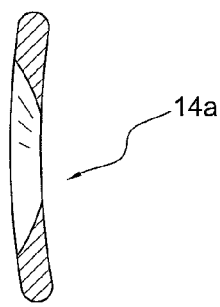
Figure 9:
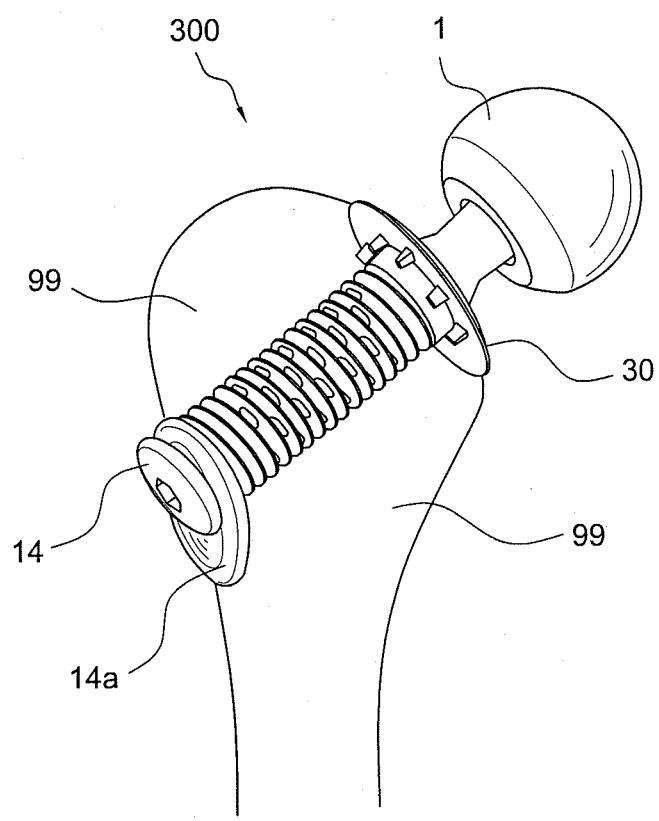
FIG. 9 illustrates a simulated, schematic view of a femur with the femoral implant of FIG. 6 implanted (i.e., with the femoral implant consisting of a femoral head (engages the cage screw), base plate, cage screw, and external lateral fixation)
Figure 10:
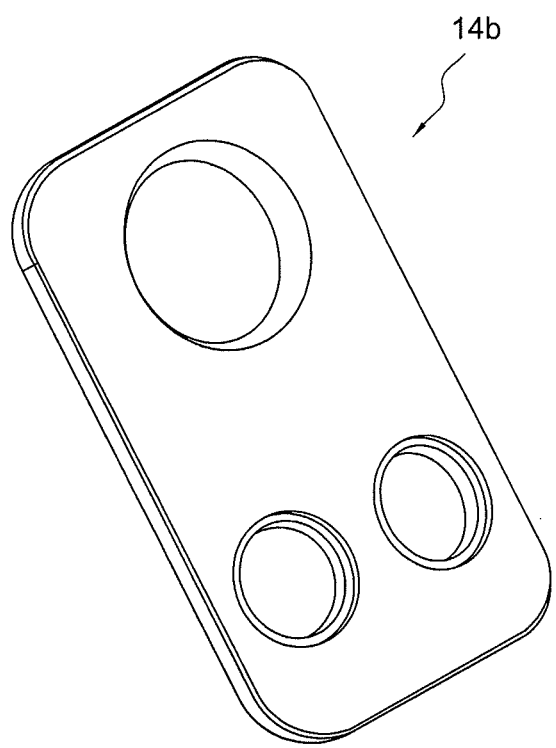
FIG. 10 is a perspective view of a plate used for lateral fixation.

Femoral implant 10, 10a may optionally include device(s) for lateral fixation, for example screw(s) for lateral fixation. In one embodiment, the screw may be an internal screw 4 (FIG. 1B). Internal screw 4 can be a screw with a single continuous thread pitch, or can be a screw with different thread pitches to allow for compression or distraction of construct to the lateral cortex, or can be a self-tapping screw, or can be a cannulated screw guided by a drill pin. In another embodiment, the screw is an external screw 14. External screw 14 may be a stand alone screw (FIGS. 8E and 8F) which may be used with washer 14a (FIGS. 8A-8D), as shown in FIGS. 6 and 9. Alternatively, external screw 14 may be used with a plate 14b for lateral fixation (FIG. 10).

FIG. 1C illustrates a simulated view of femur 99 with femoral implant 10 of the present invention, consisting of cage screw 2, base plate 3 including a neck, screw 4 for lateral fixation, and femoral head 1, and inserted into the femur 99. The femoral head engages the base plate (through the head engaging surface 3a, 13a of the base plate 3) but not the cage screw 2. Internal screw 4 for lateral fixation may exit the cortical bone (as shown in FIG. 1C) or may be wholly contained within the femur.

FIGS. 3A-4B illustrate views of another exemplary femoral implant 100, 100a consisting of cage screw 2, base plate 3 and femoral head 1.

Cage screw 2 of femoral implant 100, 100a is similar to cage screw 2 of femoral implant 10, 10a, and can be fenestrated, provided with a plurality of fenestrations or holes, and/or can be porous coated at strategic locations. The cage screw 2 itself can be used as lateral fixation (provided with cannulation or without cannulation) by inserting the distal end.

Base plate 3 of femoral implant 100, 100a is similar to base plate 3 of femoral implant 10, 10a, and may have various configurations. In one embodiment, the base plate 3 is tapered and contains femoral head mating (head engaging) surface 3a, neck 3b (of different diameters and/or lengths), and base 3c (FIGS. 3A-3I). Base plate 3 can further include a key/tab 3e for anti-rotation; can include extensions (spikes or protuberances) 3d extending from the base 3c to engage into bone; can include grooves/texture/threads 3f on the surface for engaging/locking of the femoral head; can include an engagement mechanism for engaging the femoral head in the form of a Morse taper, for example; and can include a porous backing on the base.

Figure 4A:
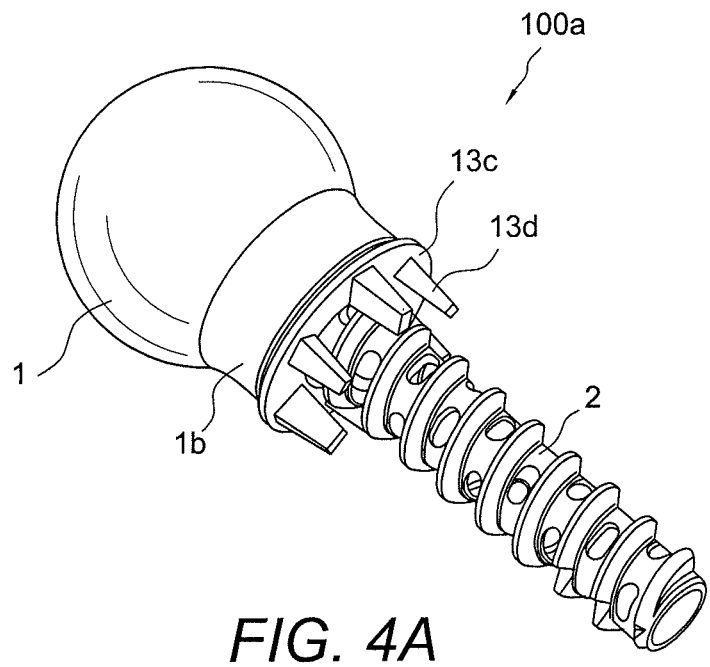
FIG. 4A illustrates a perspective view of a femoral implant according to a fourth embodiment of the present invention (with the femoral implant consisting of a cage screw, base plate, and femoral head with neck)
Figure 4B:
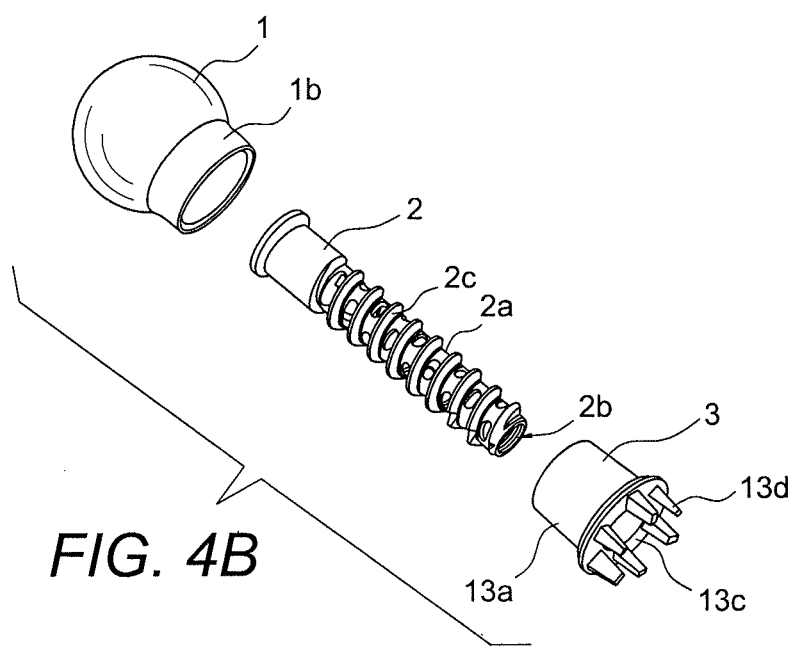
FIG. 4B illustrates an exploded view of the femoral implant of FIG. 4A.

In another embodiment, the base plate 3 contains femoral head mating surface 13a and base 13c (FIGS. 4A and 4B). Base plate 3 can further include a key/tab 3e for anti-rotation; can include extensions (spikes or protuberances) 13d extending from the base 13c; can include grooves/texture/threads 13f on the head engaging surface for locking of the head; can include an engagement mechanism for engaging the femoral head in the form of a Morse taper, for example; and can include a porous backing on the base.

Femoral head 1 of femoral implant 100, 100a is similar to femoral head 1 of femoral implant 10, 10a, may be provided with or without offset, and may be provided with a head and neck 1b combined (FIG. 4B).

Figure 3A:
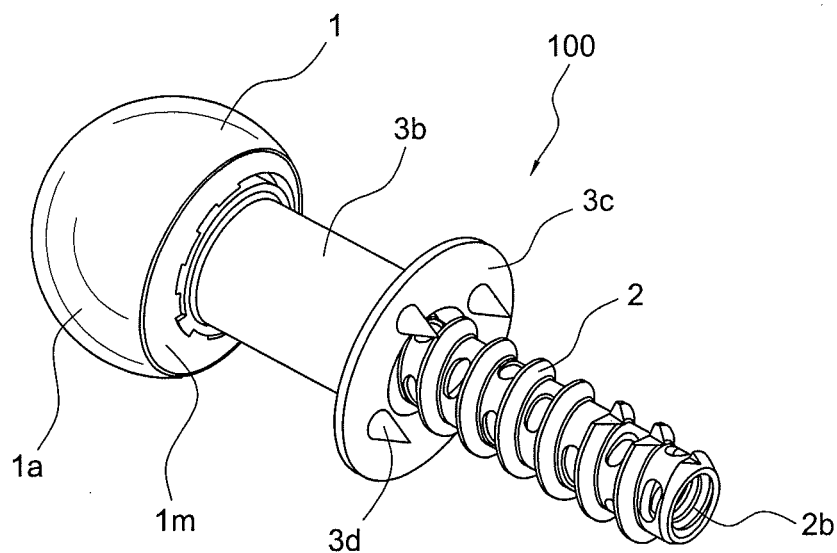
FIG. 3A illustrates a perspective view of a femoral implant according to a third embodiment of the present invention (with the femoral implant consisting of a cage screw, base plate including a neck, and femoral head)
Figure 3B:
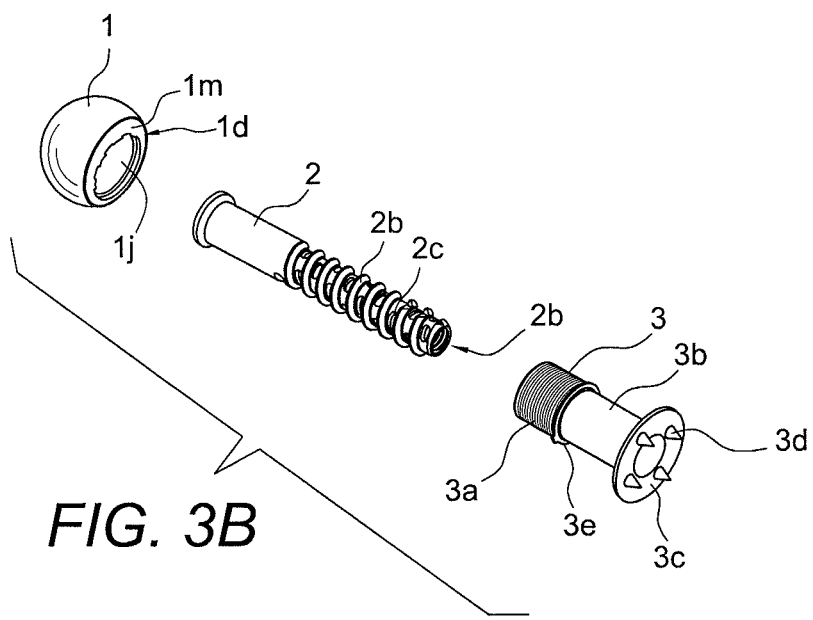
FIG. 3B illustrates an exploded view of the femoral implant of FIG. 3A.
Figure 3C:
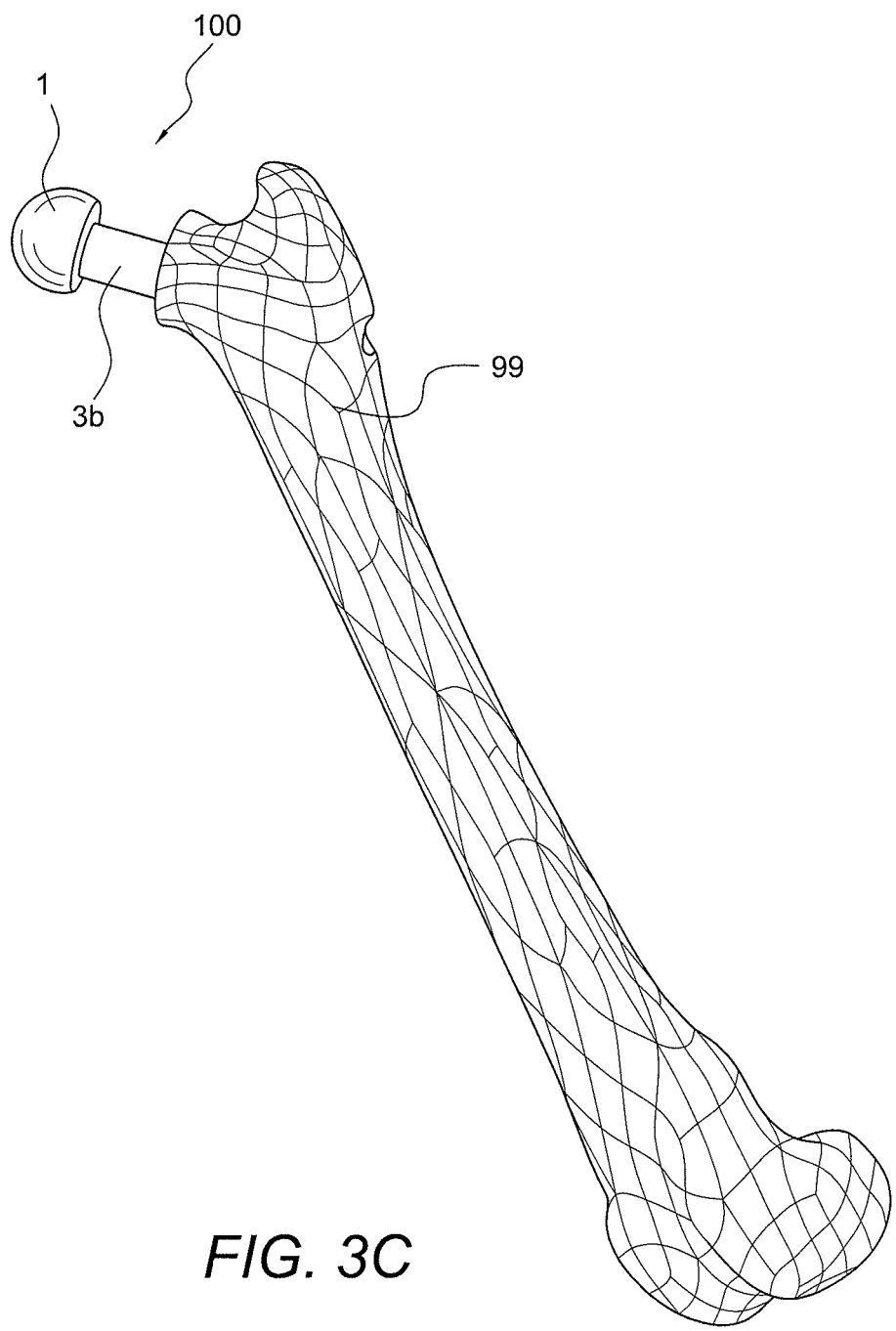
FIG. 3C illustrates a simulated femoral implant (consisting of a cage screw, base plate including a neck, and femoral head) inserted into the femur.

FIG. 3C illustrates a simulated view of femur 99 with femoral implant 100 of the present invention, consisting of cage screw 2, base plate 3 including a neck 3b (without a screw for lateral fixation) and femoral head 1 inserted into the femur 99. The femoral head 1 engages the neck 3b of the base plate 3 and not the cage screw 2.

Figure 3D:
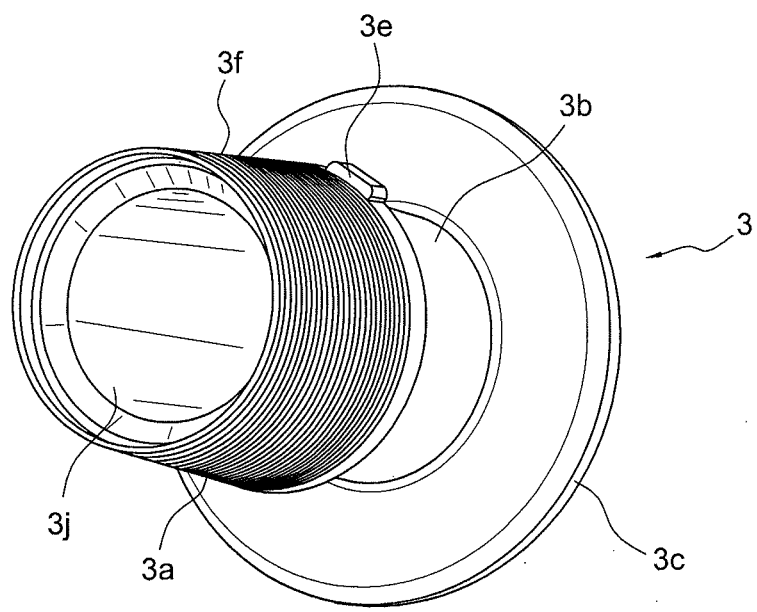
FIG. 3D illustrates a perspective view of the base plate of FIG. 3A (with a countersunk to receive the screw head)
Figure 3E:
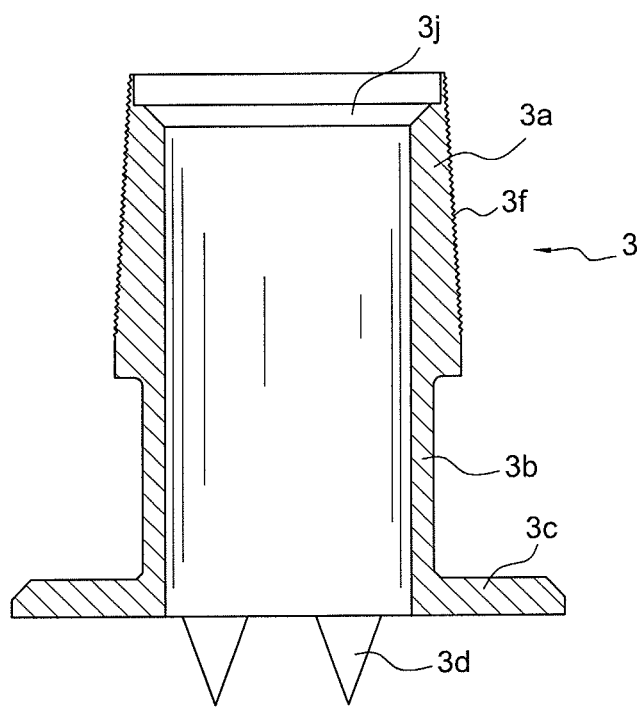
FIG. 3E illustrates a cross-sectional view of the base plate of FIG. 3D.
Figure 3F:
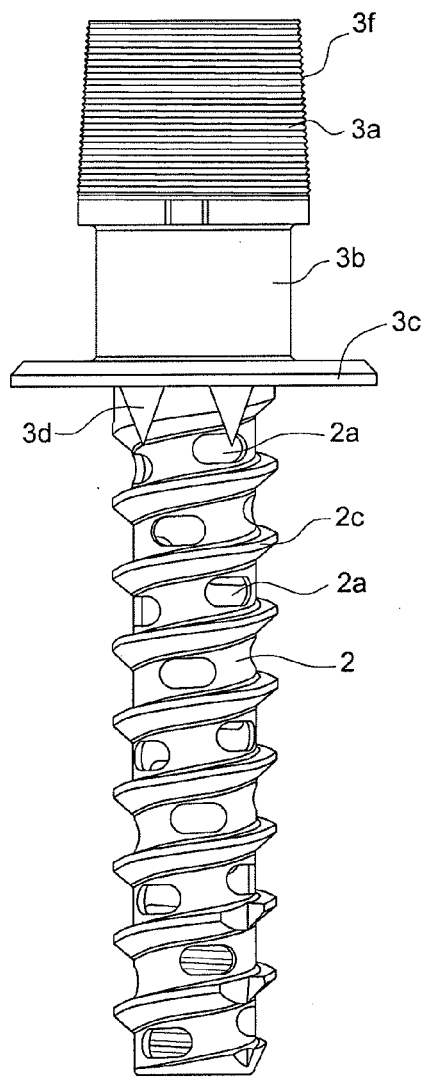
FIG. 3F illustrates a front view of the base plate of FIG. 3A housing the screw.
Figure 3G:
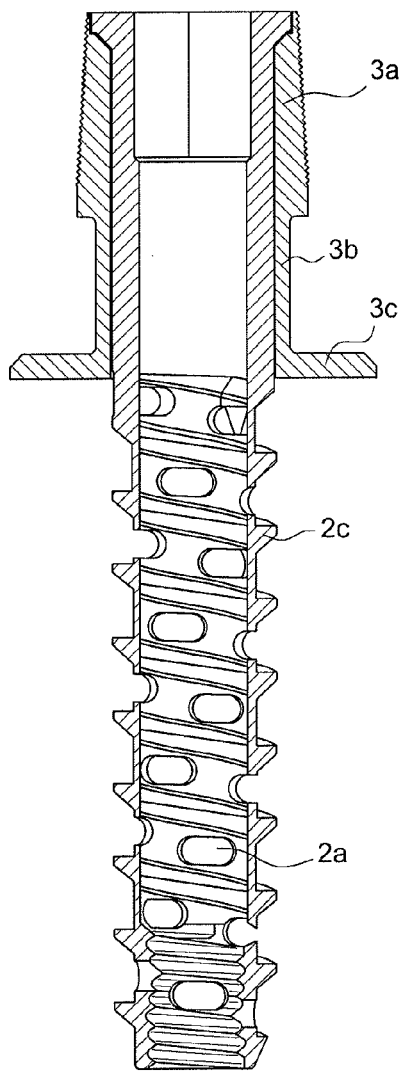
FIG. 3G illustrates a cross-sectional view of the base plate and screw of FIG. 3F.
Figure 3H:
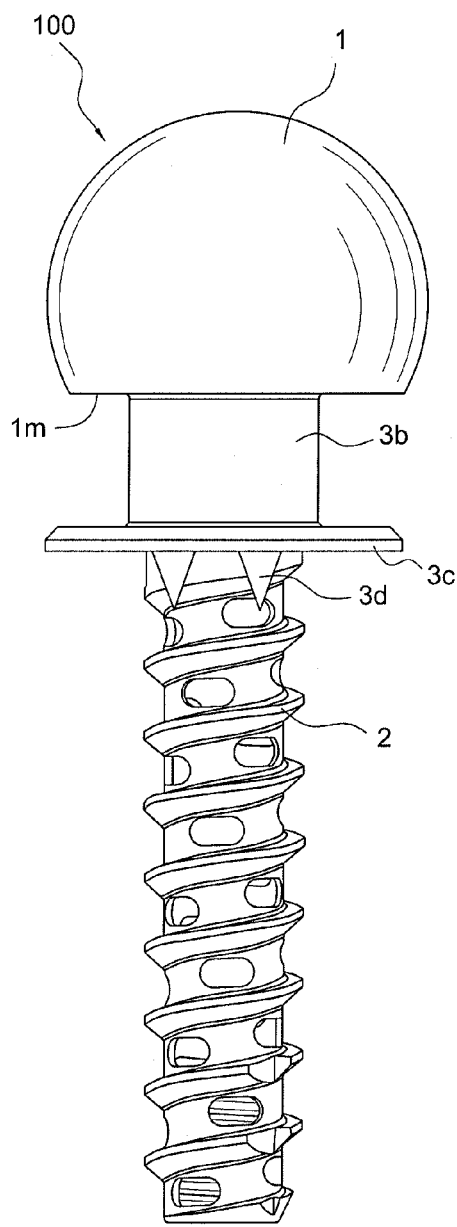
FIG. 3H illustrates a front view of the assembled femoral implant of FIG. 3A (an assembly of offset femoral head, base plate with neck, and screw)
Figure 3I:
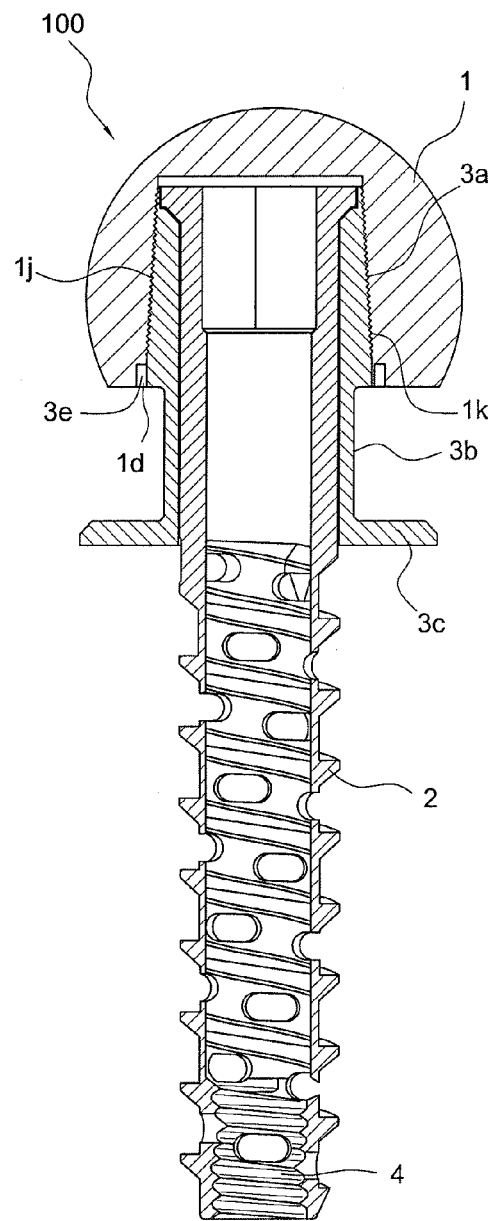
FIG. 3I illustrates a cross-sectional view of the femoral implant of FIG. 3H.

FIGS. 3D-3I illustrate additional views of the base plate 3, cage screw 2 and femoral head 1 of the femoral implant 100 of FIG. 3A, illustrating in more details the characteristics of these components and the way they are assembled (i.e., in progression of how the femoral implant 100 is assembled). FIGS. 3D and 3E illustrate tapered head engaging surface 3a with countersunk hole 3j to receive the cage screw 2. FIGS. 3F and 3G illustrate the way the base plate 3 houses cage screw 2. FIGS. 3H and 3I illustrate the way femoral head 1 (in this particular case, an offset femoral head 1) engages the tapered head engaging surface 3a of the base plate 3, with tab 1d of the femoral head fitting/engaging the tab 3e of the base plate 3.

Figures 5A, 5B:
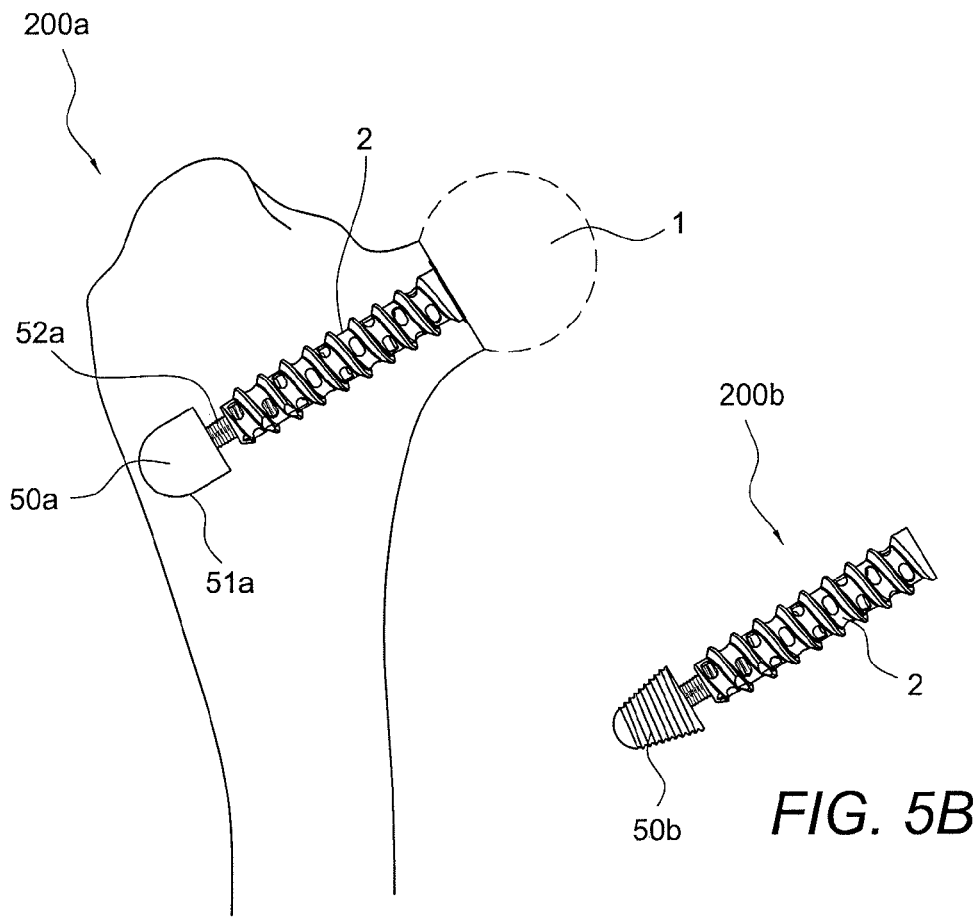
FIG. 5A is a schematic view of femur with an exemplary femoral implant and with a device that extends from the cage screw for minimizing micro-motion.
FIG. 5B is a schematic view of another device that extends from the cage screw for minimizing micro-motion.

FIGS. 5A and 5B illustrate femoral implant 200a, 200b of the present invention with device 50a, 50b (extension device 50a, 50b) extending from the cage screw 2 for minimizing micro motion and preventing the cage screw from shifting upon and after insertion. Device 50a, 50b extends from the opposite end of the screw head, i.e., from a distal end of the cage screw 2 and acts as a stop. According to an exemplary embodiment (shown in FIG. 5A), the device 50a may be an anchor-type device with a smooth outer surface 51a (for increased osseointegration) and communicates with the cage screw 2 (by a threaded region 52a corresponding to a threaded opening in the cage screw). In another embodiment (shown in FIG. 5B), the device 50b is similar to a screw, providing a strong anchor within the bone tunnel or socket. Device 50a, 50b is integral to the cage screw 2, i.e device 50a, 50b is screwed to the cage screw prior to insertion of the screw 2/device 50a, 50b assembly through the base plate 3 and into the femoral tunnel or socket.

FIG. 6 illustrates an exploded view of a femoral implant 300 according to a fifth embodiment of the present invention. Femoral implant 300 consists of a cage screw 2, a base plate 30, femoral head 1, an external screw 14 and an external washer 14a for lateral fixation with washer 14a. FIGS. 7A-7E illustrate various views of the base plate 30 of FIG. 6 that is configured to situate the cage screw 2 on the base plate. As in the previous embodiments, the outer diameter of the base plate is about equal to the outer diameter of opening 1f of the femoral head 1 and has a thickness of about 1 to about 5 mm, more preferably of about 2 mm to ensure secure placement of the base plate over the remaining, cut surface of the resected femoral head. In this embodiment, the femoral head directly engages the cage screw.

Figure 8D:
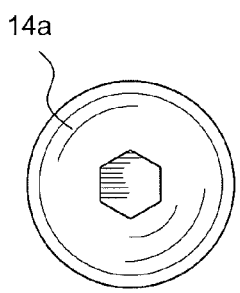
Figure 8E:
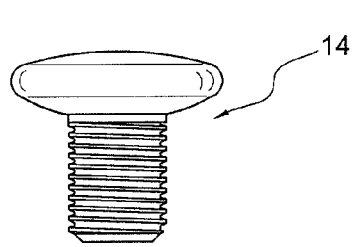
Figure 8F:
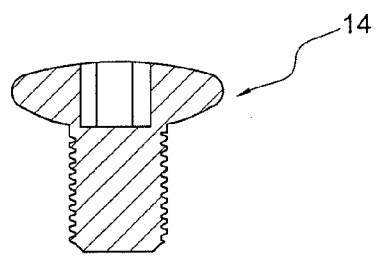

Details of the screw 14 are depicted in FIGS. 8D-8F. Details of the washer 14a are depicted in FIGS. 8A-8C. FIG. 9 illustrates a simulated, schematic view of a femur 99 with the femoral implant 300 of FIG. 6 implanted (i.e., with the femoral implant consisting of a femoral head, base plate, cage screw, and external lateral fixation).

The femoral implant of the present invention may be manufactured from titanium alloy or other metallic materials. The femoral head 1 may be manufactured from materials similar to (or different from) those of the screw 2 and base 3. For example, the cage screw 2 may be made of titanium or titanium alloy, the femoral head 1 may be made of cobalt chrome, and the base plate 3 may be made of titanium or titanium alloy.

Figure 27:
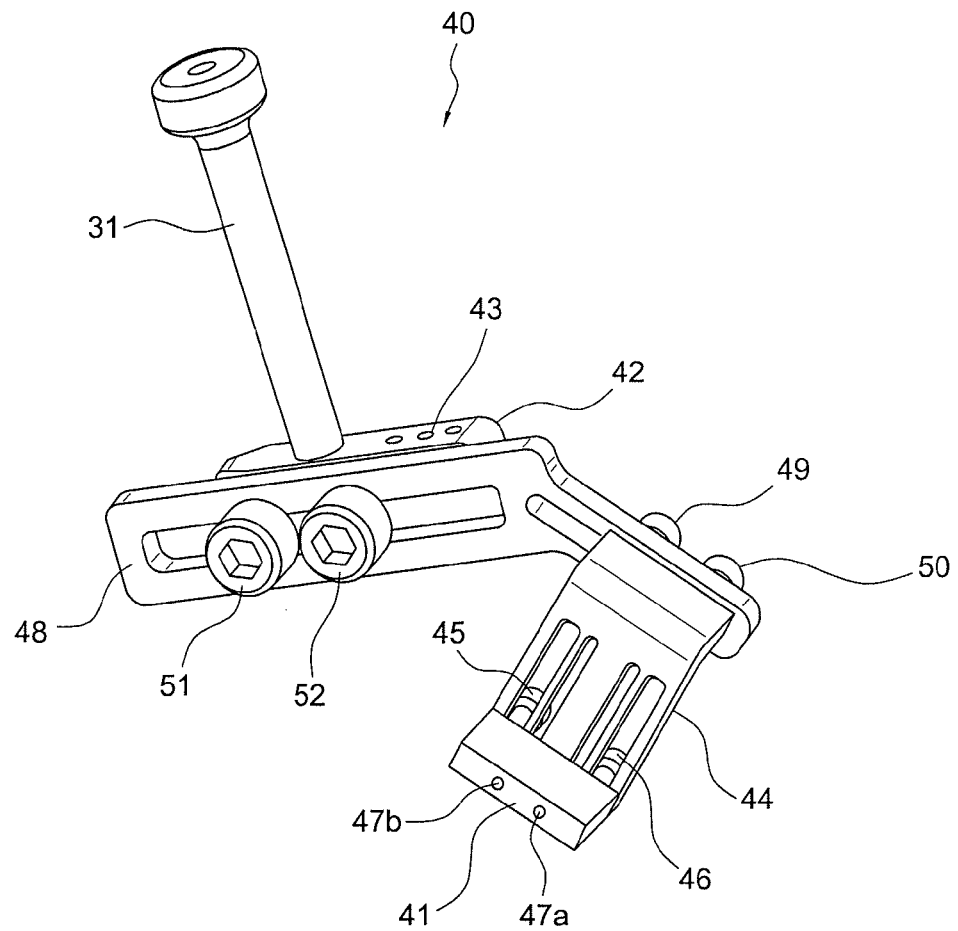
FIG. 27 illustrates an assembled view of a head resection guide according to an embodiment of the present invention.
Figure 28:
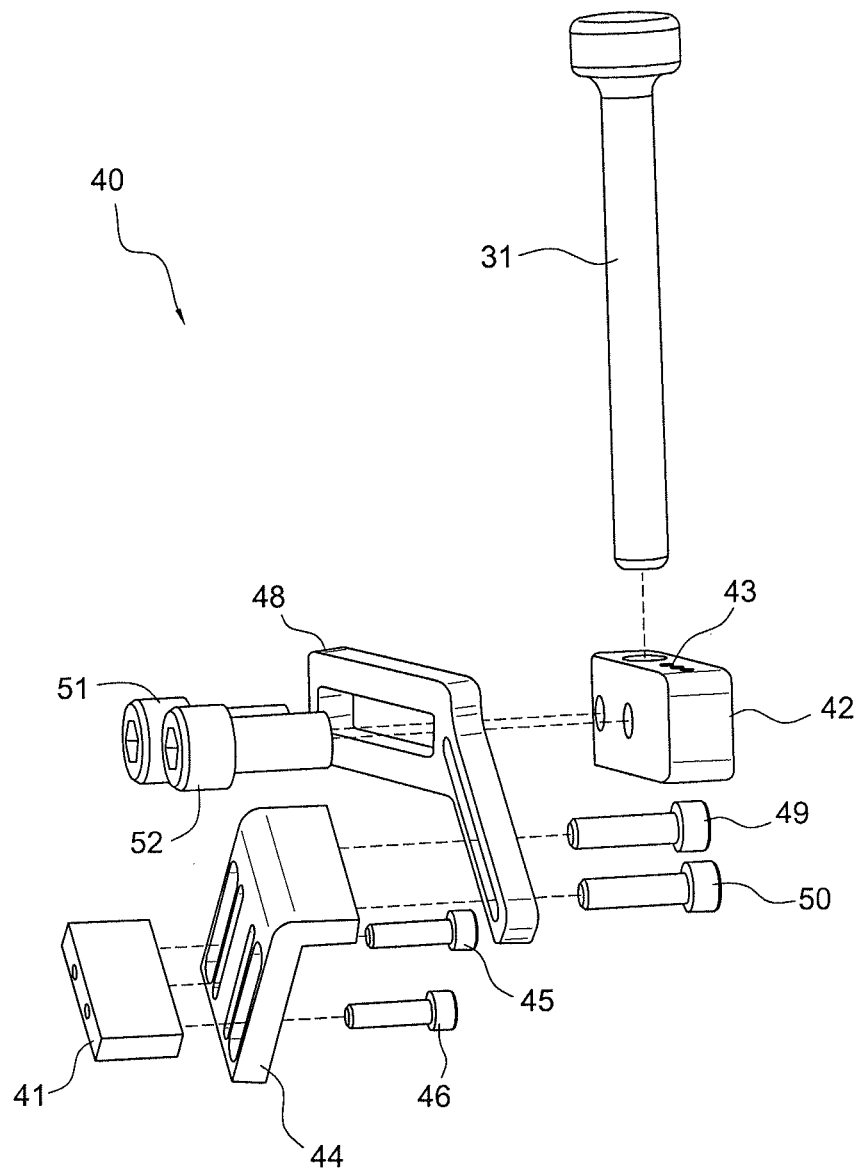
FIG. 28 illustrates an exploded view of a head resection guide assembly of FIG. 27.

FIGS. 11-26 illustrate subsequent steps of a method of replacing a portion of the femoral head with a hip prosthesis of the present invention. FIGS. 27 and 28 illustrate various views of a head resection guide according to an embodiment of the present invention and used in the method of FIGS. 11-26.

The surgical technique described below provides a single incision; a one side approach; conserves the medullary canal by reaming only a small portion, allowing for revision; and provides a guided approach, with reproducible results.

Figure 11:
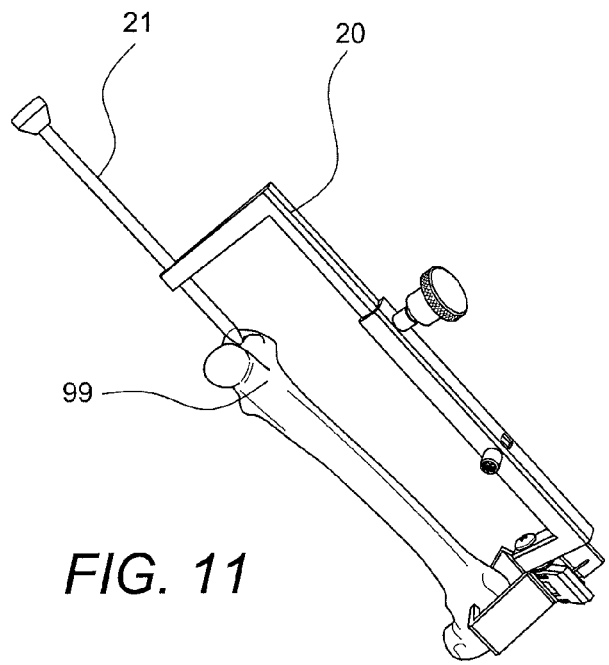
FIGS. 11-26 illustrate steps of a method of replacing a portion of the femoral head with the hip prosthesis (femoral implant) of the present invention.
Figure 12:
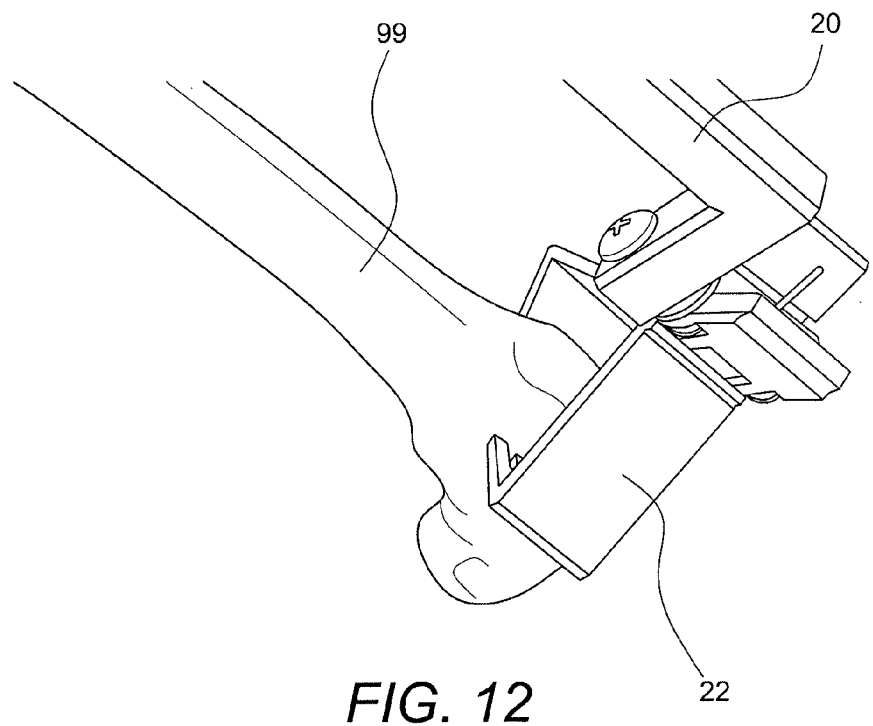

A method to implant the minimally invasive total hip replacement of the present invention comprises the following steps:

Use an alignment guide 20 to place a drill pin down the intramedullary canal of the femur 99 (FIGS. 11 and 12). The alignment guide 20 has a clamp 22 to fit around the base (distal end) of the femur 99. The alignment guide is extended to rest on proximal end of femur. Adjust the drill sleeve 21 to rest against the top of the femur, preferably parallel to the shaft and centered on the shaft. FIG. 11 shows the alignment guide positioned in place for placement of the drill tip. FIG. 12 shows a clamp 22 of the guide 20 where the drill pin will exit the femur.

Insert the drill pin 30 through the drill sleeve 21 into femur 99. Remove the alignment guide 20 from the femur leaving the drill pin in place.

Figure 13:
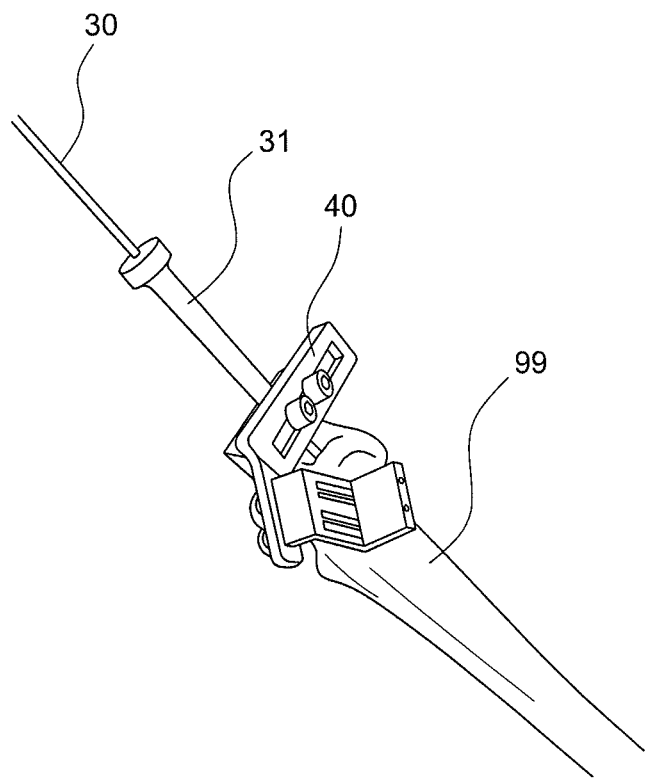

Place the sleeve 31 of the head resection guide 40 over the drill pin (FIG. 13). Details of the head resection guide 40 are shown in FIGS. 27 and 28 wherein the resection guide 40 includes a sleeve 31, a base 42, an anti-rotation pin hole 43, a sliding arm 48, locking screws 51, 52, drill pin guide arm 44, locking screws 49, 50, drill pin guide block 41, locking screws 45, 46, and drill pin holes 47a, 47b.

Figure 14:
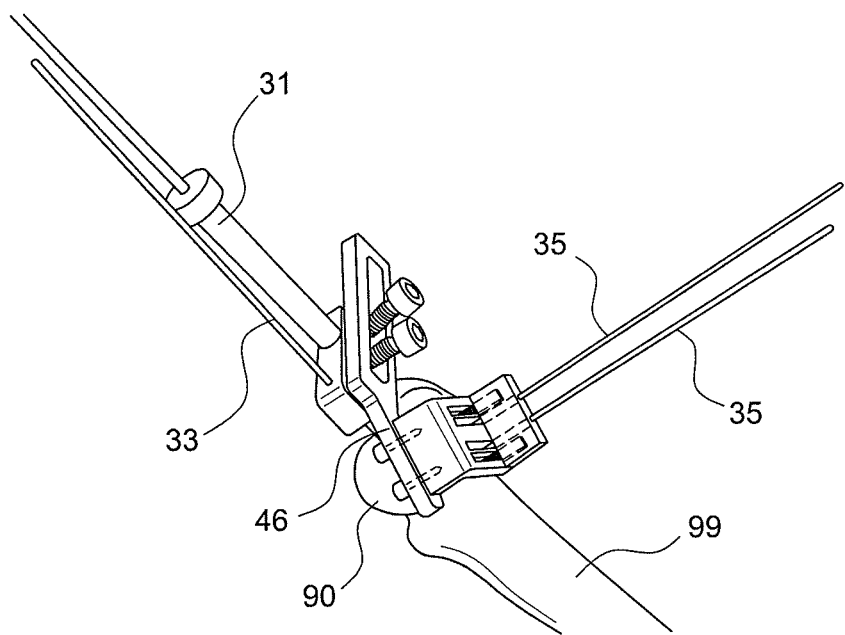

Optional: Adjust the base of the head resection guide 40 so that it is in alignment along the center of the femoral neck and the greater trochanter. Insert an anti-rotation pin 33 into the top of the femoral head 90 (FIG. 14). The anti-rotation pin 33 allows for alignment along the center of the femoral neck/head and the greater trochanter while preventing rotation. Helps to visualize the plane perpendicular to the cutting plane.

Adjust the head resection guide 40 for pin placement. Adjust sliding arm 48 in the medial direction. Once the desired position is obtained, lock screws 51, 52 in place. A 90 degree guide is shown but other angled options are contemplated. Slide the drill pin guide arm 44 until drill holes 47a, 47b are positioned, centered on femoral neck. Tighten locking screws 49, 50. Adjust drill pin guide block medial-laterally to be below the femoral head in the neck region. Lock the block in place by tightening screws 45, 46. Place drill pins 35 through the drill holes 47a, 47b at the desired location for resection of the femoral head 90 (FIG. 14).

Figure 15:
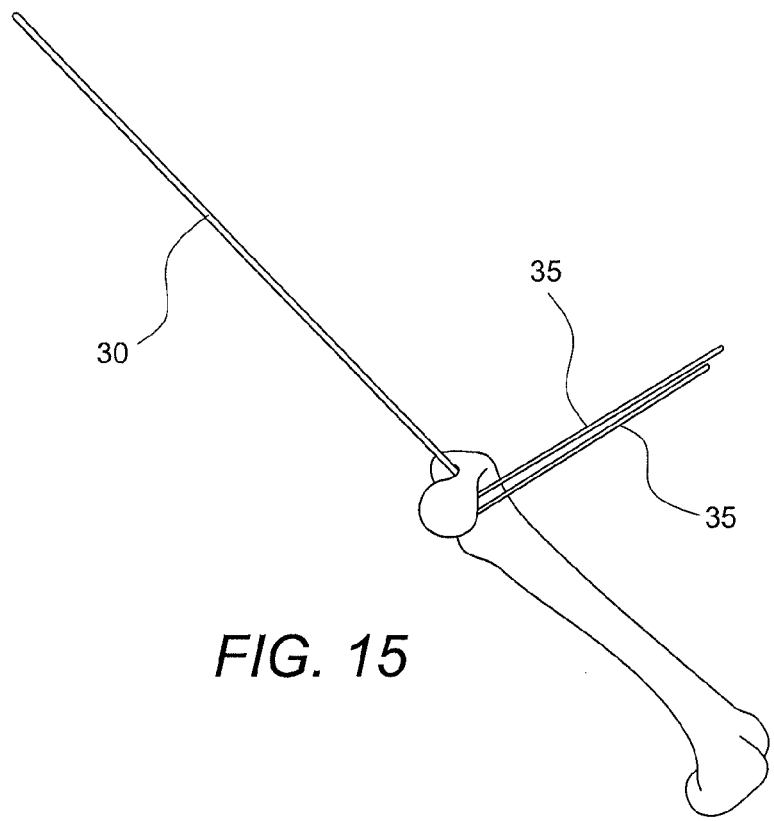
Figure 16:
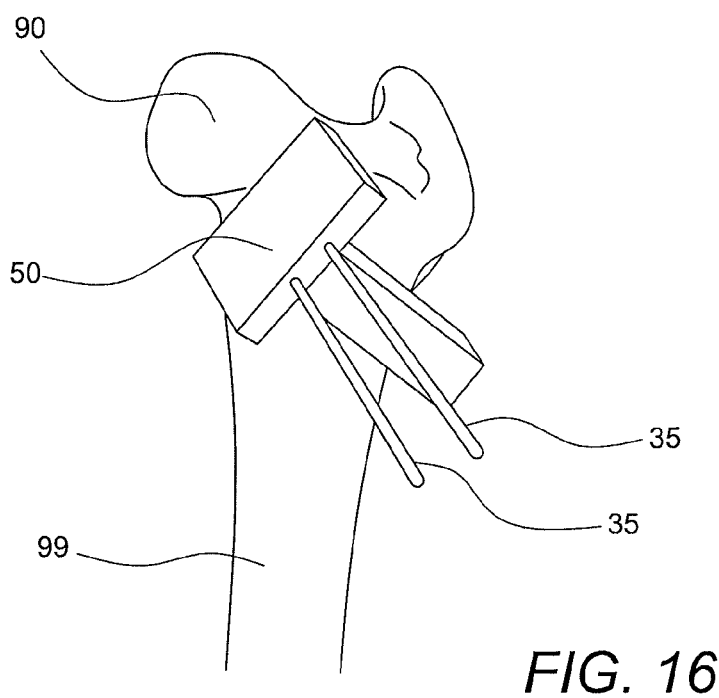
Figure 17:
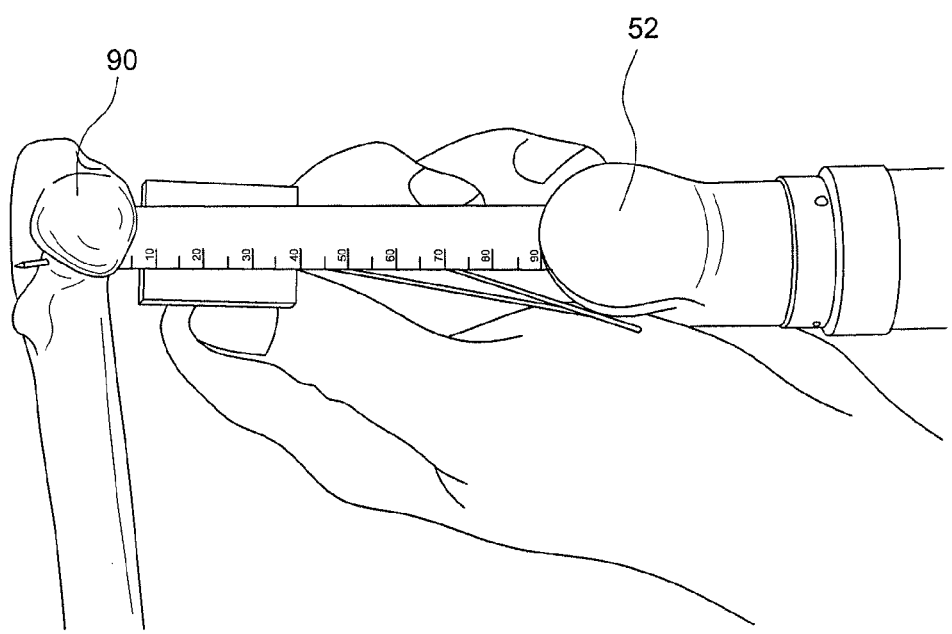
Figure 18:
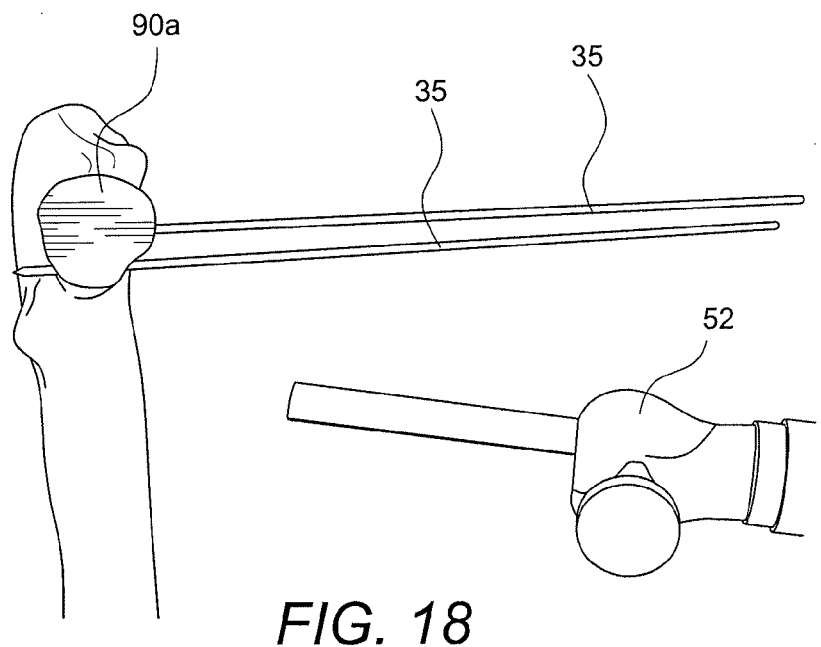

Disassemble the guide and remove the anti-rotation pin 33 leaving the drill pins 35 in place (FIG. 15). A cutting guide 50 can be used to make the cut on the femoral head 90 if desired. Place the cutting guide 50 over the drill pins 35 (FIG. 16). Optionally, the cut may be made freehand using the pins as guides.

Cut the femoral head 90 (FIGS. 17 and 18) with a cutting instrument 52 to obtain surface 90a of the cut femoral head.

Figure 19:
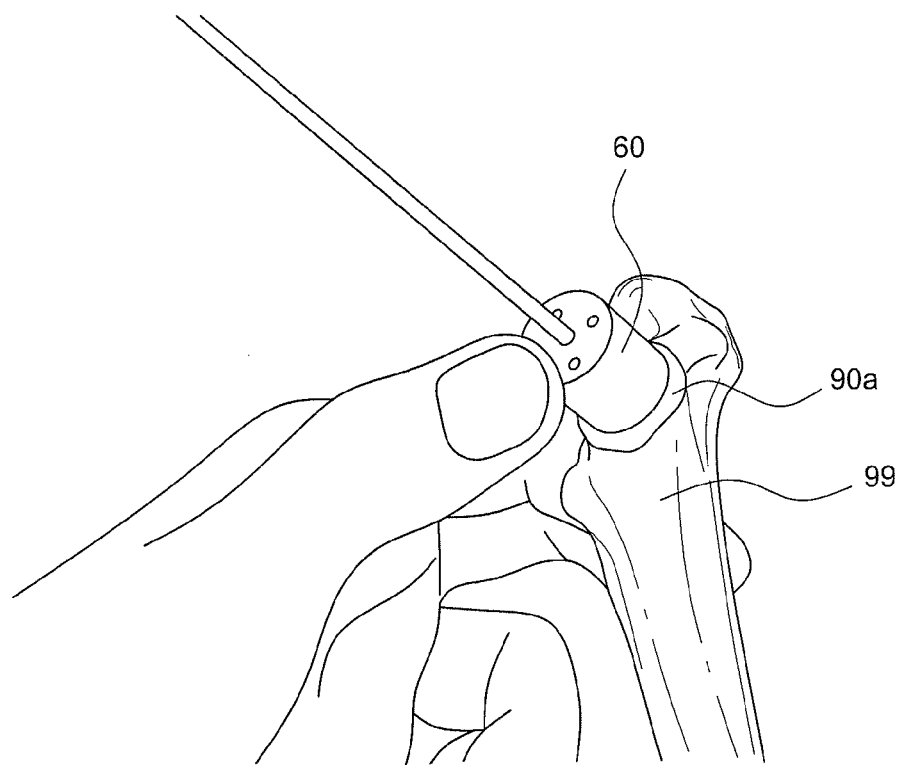

Optional: A centering guide 60 can be used to center a drill pin down the femoral neck. Place the centering guide 60 flush and centered on cut surface 90a of the femoral neck (FIG. 19). Optional: Drill through circumferential holes 61 on guide 60 to prepare pilot holes for protrusions of base plate.

Figure 20:
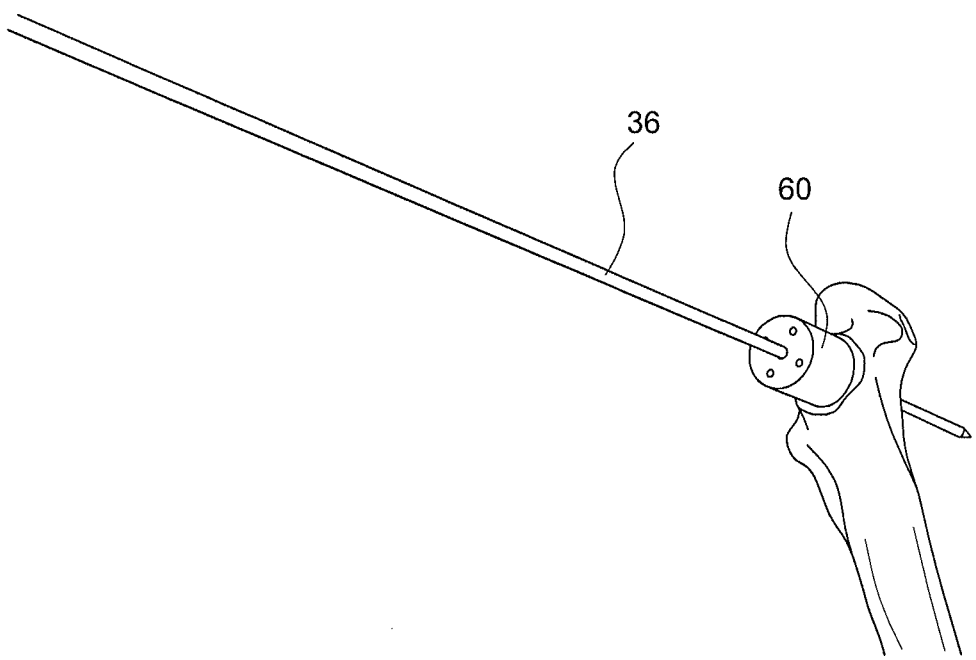

Insert a drill pin 36 down the femoral neck through opposite lateral edge (FIG. 20).

Figure 21:
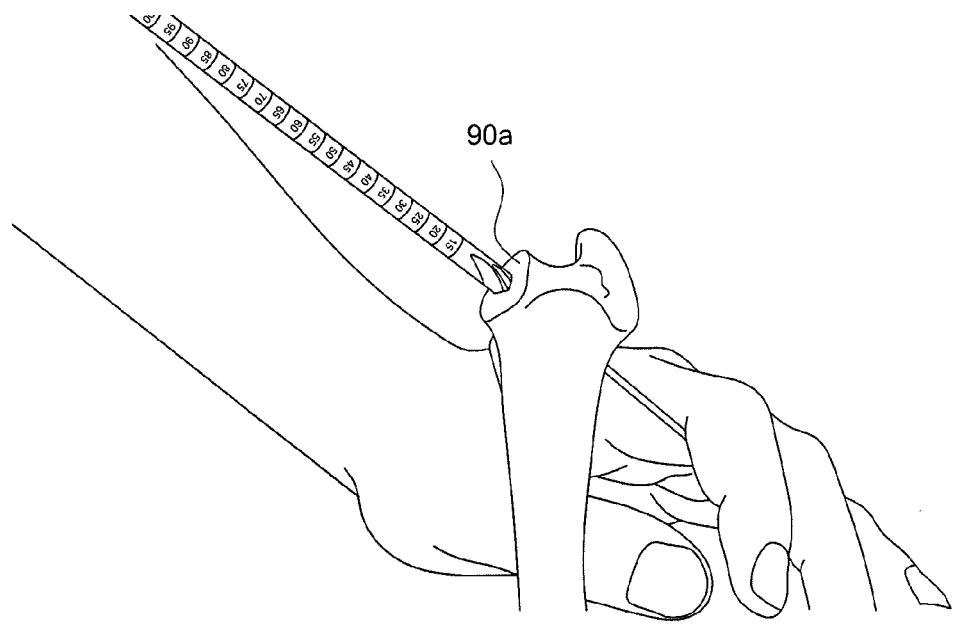

Ream the appropriate size tunnel (based on size of implant to be used) down the neck up to but not through the lateral cortex (FIG. 21).

Optional: Can ream through the lateral cortex if no other fixation is used.

Figure 22:
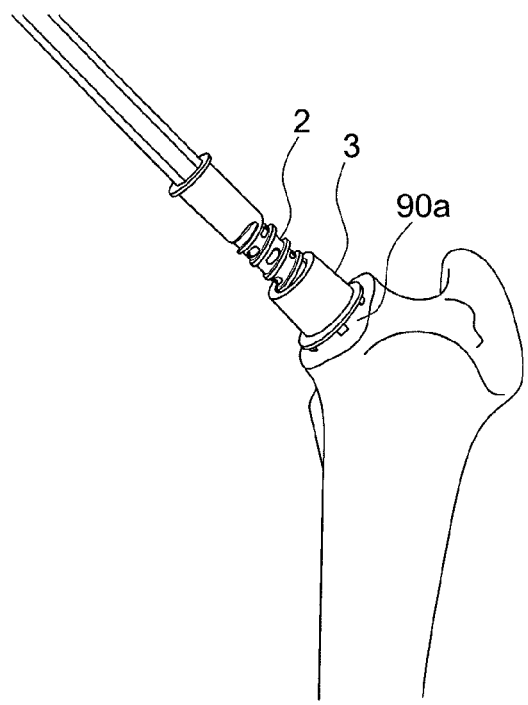
Figure 23:
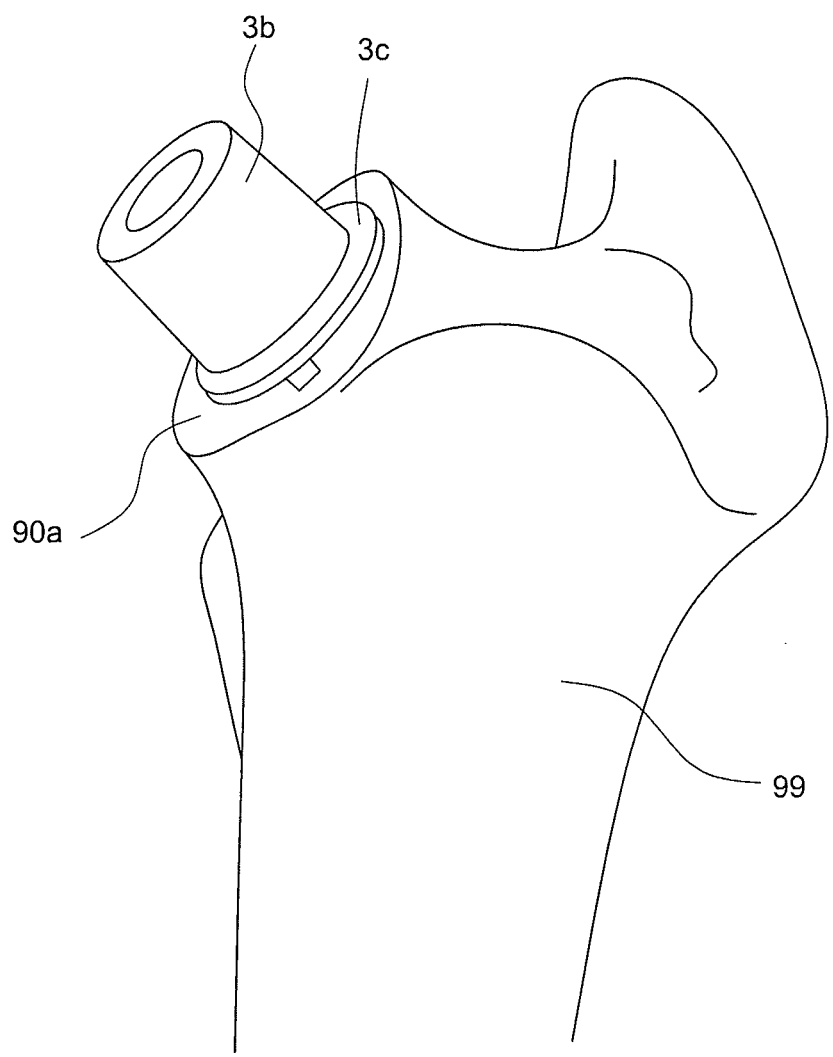

Place the base plate 3 over the reamed neck and insert the cage screw 2 through the base plate 3 until the cage screw 2 is seated flush on top of base plate (FIGS. 22 and 23). The base plate should have circumferential contact with the cortical rim.

Figure 24:
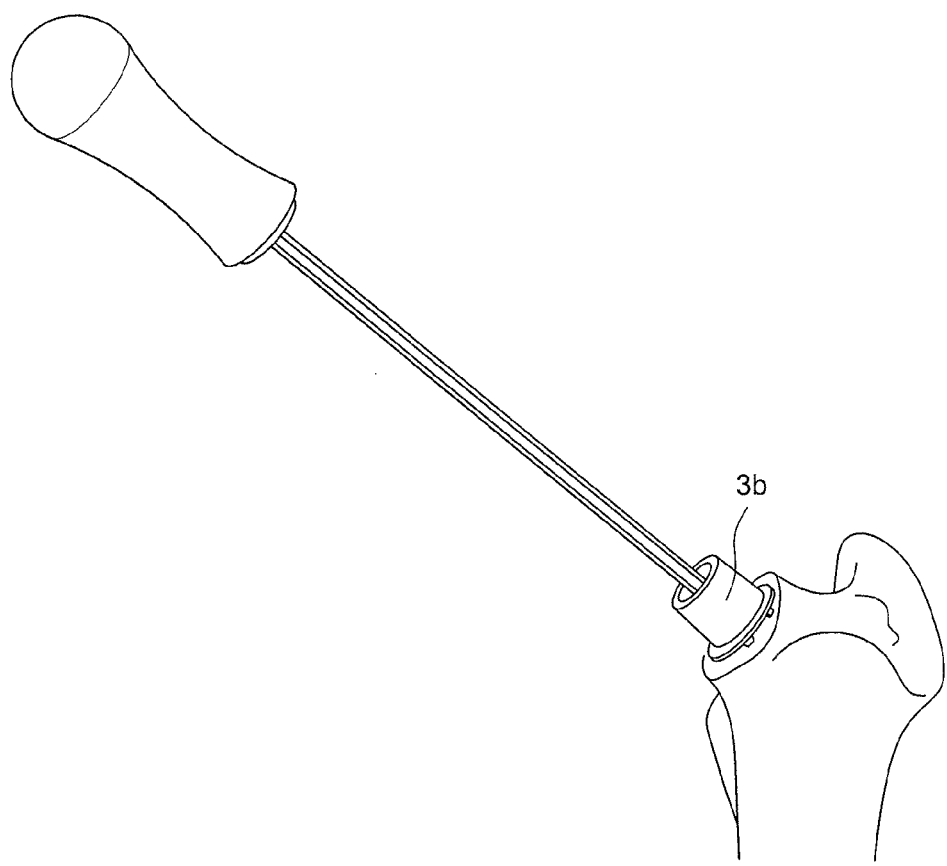
Figure 25:
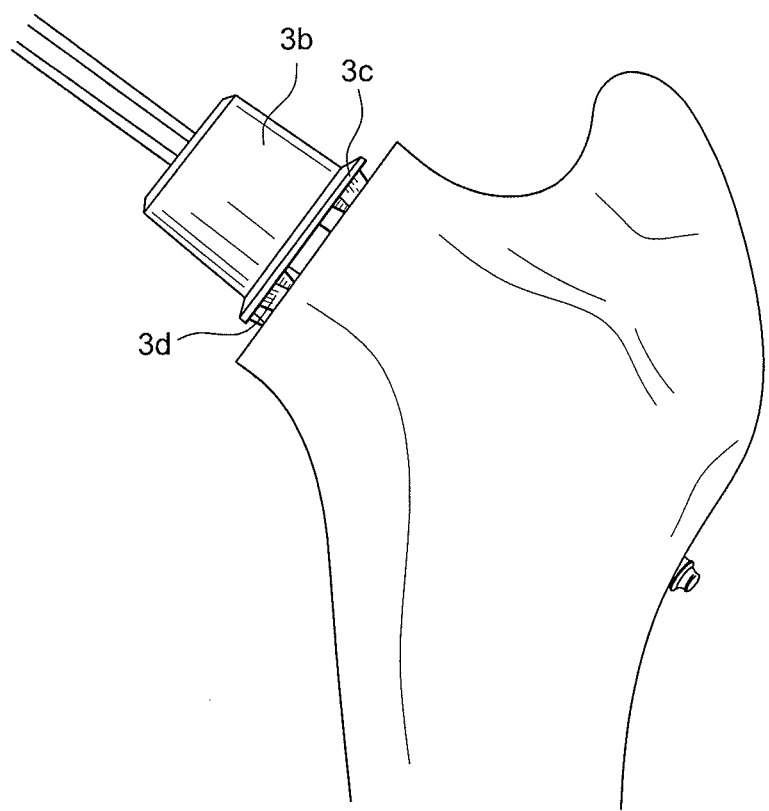

Optional: if using an implant with internal lateral screw 4, use driver to advance internal lateral screw 4 into lateral cortex (FIG. 24).

Optional: if using external lateral screw 14, make incision and insert external lateral screw 14 with washer 14a or plate 14b, if necessary.

Optional: if reamed through the lateral cortex, insert the cage screw 2 so the end comes through and engages the lateral cortex.

Optional: if using implant 200a, 200b (FIGS. 5A and 5B), insert driver through the cage screw to advance the stop to abut the lateral cortex to prevent micro-motion.

Figure 26:
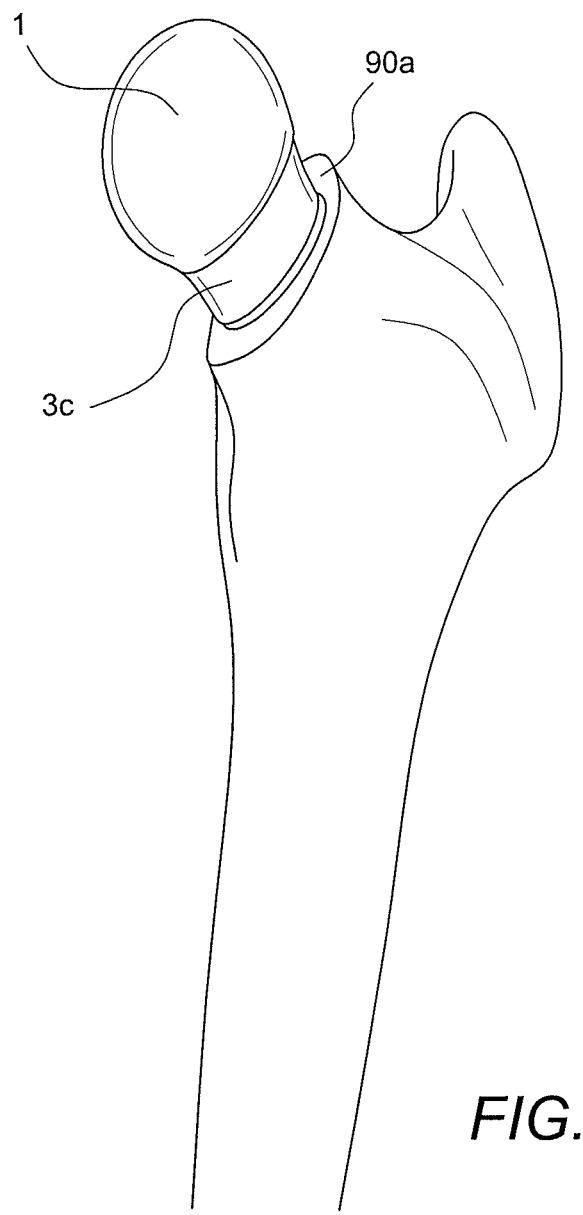

Place femoral head 1 over the base plate 3 (FIG. 26).

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A method of hip replacement, comprising the steps of:
   resecting a portion of a femoral head at a defect location;
   preparing a socket or tunnel in the defect location;
   placing a base plate of an implant over the defect location and over the socket or tunnel so that the base plate is flush with a femoral contour, the base plate including a central opening;
   subsequently, inserting a cannulated, threaded screw through the central opening and then into the socket or tunnel until a proximal end of the cannulated screw is seated flush on top of the base plate, the screw having a distal end with an internal thread;
   advancing a fixation device having a proximal end and a distal end into femoral cortex by inserting the fixation device through the cannulated, threaded screw, so that the cannulated, threaded screw receives and engages the fixation device at the internal thread, and the distal end of the cannulated, threaded screw is aligned with the proximal end of the fixation device; and
   placing a spherical head over the base plate so that the spherical head rests on the base plate.

2. The method of claim 1, wherein the cannulated threaded screw comprises a plurality of fenestrations.

3. The method of claim 1, wherein the spherical head is provided with an internal area, and wherein the base plate has a body with an outer engaging surface that engages the internal area of the spherical head when the spherical head is attached to the base plate.

* * * * *